United States Patent [19]

Donini

[11] 4,062,942

[45] Dec. 13, 1977

[54] INDUCTION OF OVULATION WITH PARTIALLY DESIALYLATED HUMAN CHORIONIC GONADOTROPIN

[75] Inventor: Pietro Donini, Rome, Italy

[73] Assignee: Serone Laboratories, Inc., Boston, Mass.

[21] Appl. No.: 658,490

[22] Filed: Feb. 17, 1976

[30] Foreign Application Priority Data

Feb. 17, 1975  Italy .................................... 48202/75

[51] Int. Cl.$^2$ ..................... A61K 35/12; A61K 35/22; A61K 35/48
[52] U.S. Cl. ..................................... 424/100; 424/105
[58] Field of Search .................. 424/95, 99, 100, 101, 424/105, 108, 177; 260/112 R

[56] References Cited

PUBLICATIONS

Physicians' Desk Reference, Med. Economics Co., Oradell, N. J., 28th Ed. 1974, pp. 576, 1344, 1355.
Tsuruhara, Endocrinology, vol. 91, 1972, pp. 296-301.
Van Hall, Endocrinology, vol. 89, July 1971, pp. 11-15.
Van Hall, Endocrinology, vol. 88, Feb. 1971, pp. 456-464.
Yang, Chem. Abs. vol. 79, 1973, Ab. No. 64010s.

*Primary Examiner*—Albert T. Meyers
*Assistant Examiner*—A. P. Fagelson
*Attorney, Agent, or Firm*—Ostrolenk, Faber, Gerb & Soffen

[57] ABSTRACT

Partially desialylated human Chorionic Gonadotropin is used after menotropin administration to induce ovulation.

5 Claims, No Drawings

INDUCTION OF OVULATION WITH PARTIALLY DESIALYLATED HUMAN CHORIONIC GONADOTROPIN

This invention relates to medicaments and, more particularly, to the therapeutic use of partially desialylated human chorionic gonadotropin.

Human chorionic gonadotropin (hCG) is a hormone occuring in the urine of pregnant women, produced by the throphoblast, that stimulates the production of progesterone by the corpus luteum. Chemically, hCG is a glycoprotein having the molecular weight of about 37,000. Just like the other glycoprotein hormones such as, for example, Follicle Stimulating Hormone (FSH), Luteinizing Hormone (LH), Thyroid Stimulating Hormone (TSH), and so on, hCG contains terminal sialic acid (N-acetyl-neuraminic acid or NANA) residues.

Human chorionic gonadotropin has been extensively employed in sequential therapy with human gonadotropins for the purpose of inducing ovulation, thanks to the fact that its biological properties are very close to those of LH, and that hCG is much more easily available than LH. In addition, hCG has sometimes proven even more effective than LH itself in the treatment of infertility; see Gemzell, C., Rec. Progr. Hormone Res. 21, 179 (1965). Anovulatory infertile women in whom the cause of anovulation is secondary and is not due to primary ovarian failure can be made fertile by means of a first treatment with an hMG (human Menopausal Gonadotropin) preparation such as, for example, that marketed under the trademark "Pergonal," which is a purified preparation of gonadotropins extracted from the urine of postmenopausal women (menotropins). The treatment, consisting of the administration of the said preparation in an adequate amount for 9 to 12 days, in most instances results only in follicular growth and maturation. In order to effect ovulation, hCG must be given following the administrtion of hMG when clinical and laboratory tests indicate that sufficient follicular maturation has occured.

Although the above described sequential menotropins-hCG therapy has proven highly effective in treating infertility in women, there are several hazards associated with the therapy, among which overstimulation of the ovary and multiple births should be particularly mentioned.

In order to minimize the hazard of an abnormal ovarian enlargement associated with the therapy, the lowest therapeutic doses consistent with expectation of good results have been used. Studies performed using low doses of menotropins and, more importantly, hCG have shown that the incidence of the hyperstimulation syndrome is of about 0.4%, whreas hyperstimulation occurs in 1.3% of patients when higher doses are administered.

On the other hand, the lower are the administered doses, the less is the likelihood that good results (that is, ovulation and pregnancy) are obtained.

The hazard of multiple pregnancy is even more substantial. Of the pregnancies following therapy with menotropins and hCG, 80% have resulted in single births and 20% in multiple births, most of which have been twins.

Therefore, the need exists of a new therapeutic means which avoids or minimizes the above-mentioned hazards. The investigations carried out in accordance with this invention have shown that partially desialylated hCG constitutes such a therapeutic means when substituted for intact hCG in the usual menotropins-hCG sequential therapy.

Accordingly, this invention provided a new medicament suitable for use in inducing ovulation which comprises partially desialylated hCG, as well as a method for inducing ovulation without the hazards of overstimulation of the ovary and multiple births, which comprises the sequential administration of menotropins and desialylated hCG. The exact role of the terminal sialic acid residues that have been shown to be present in the glycoproteins has not yet been clearly shown. However, it has experimentally been found that progressive desialylation is accompanied by an increase of the clearance rate of the glycoprotein from plasma as well as by a decrease of its biological activity. It has also been found that, although the biological activity of a glycoprotein decreases as the degree of desialylation progressively increases, its immunological activity does not significantly change.

The above finding have led to the hypothesis that the main role of the terminal sialic acid residues of glycoproteins is that of prolonging the survival of the hormones during metabolism in vivo.

In fact, the decrease of biological activity following desialylation is more strictly correlated with the decrease of plasma half-life than with the decrease of the intrinsic biological activity of the glycoprotein at the target cell-level.

In consideration of several factors including a convenient balance between the desired clearance rate of partially desilylated hCG and the decrease of its biological activity accompanying desialylation, a preferred degree of desialylation has been found to be comprised between the limits of 15 and 35%. Accordingly, this invention provides, in one of its preferred aspects. partially desialylated hCG having a degree of desialylation of from 15 to 35% as a therapeutic means which is particularly suitable for inducing ovulation when substituted for intact hCG in the sequential menotropins-hCG therapy.

As used herein, hCG having a given (e.g., 20%) degree of desialylation, or "20% desialylated hCG," means hCG from which 20% of the total NANA content has been removed.

Free NANA can be determined by the colorimetric assay described by L. Warren in J. Biol. Chem. 234,1971 (1959). Bound NANA can be determined by the same method after acid digestion of hCG or partially desialylated hCG with $H_2SO_4$.

hCG can be partially or totally desialylated in accordance with the method described by Van Hall et al. in Endocrinology 88,456 (1971).

A more preferably method for desialylating hCG is that described in copending U.S. patent application Ser. No. 487,722 entitled "Desialylation of glycoproteins." By this preferred method, desialylated glycoproteins, including hCG, having the exact desired degree of desialylation are prepared by incubating the glycoprotein with neuraminidase coupled to a solid matrix and removing the neuraminidase-solid matrix at the exact desired time.

Neuraminidase is an enzyme produced by Clostridium perfringens, that has been widely used for removing sialic acid residues from glycoproteins. Neuraminidase is used also in the Van Hall et al. method referred to above.

A specific method used herein for determining the luteinizing biological activities of LH, intact hCG and partially desialylated hCG is the Ovarian Ascorbic Acid Depletion (O.A.A.D.) described in A.F. Parlow, Human Pituitary Gonadotropins, page 300, Albert Editor, published by Charles C. Thomas (1961).

The known methods based on the ovary and uterus weight increase of 21 day old, impuberal, female rats can be used as well.

Whenever, in the present specification and claims, reference is made to the specific potency as expressed in International Units (I.U.) per mg of a preparation of any of the above mentioned hormones, International Units of biological activity are meant. The 2nd IRP (International Reference Preparation) of hCG is the standard reference preparation on the basis of which the biological activities are calculated.

Plasma half-lives of 25% desialylated hCG, human LH and intact hCG were determined in rats according to the following experimental procedure.

Twelve female, 50 to 60 day old Sprague-Dawley rats having the average weight of 200 g were divided in three groups of four, anaesthesized with 250 mg per kg body weight of phenobarbital and heparinized.

Each rat then received a single injection in the jugular vein of 800 nanograms of the following hormone dissolved in 0.1 ml saline:

Rats of the first group: human LH (11,500 I.U./mg)
Rats of the second group: hCG (5200 I.U./mg)
Rats of the third group: 25% desialylated hCG (5200 I.U./mg).

The blood was collected from carotid 1-3-5-10-20-30-45-60-90-120 minutes after the injection. The blood samples were centrifuged for 20 min at 1000 rpm and at 4° C and the hCG or LH content of each plasma sample was determined by radioimmunoassay.

The plasma half-lives ($t \frac{1}{2}$) were calculated from the obtained curves.

A similar experiment was carried out by injecting the same hormones subcutaneously in three more groups of rats. Rats were as follows:

| Hormone | t 1/2 intraveneously | subcutaneously |
|---|---|---|
| human LH | 3 min | 55 min |
| hCG | 17 min | 100 min |
| 25% desialylated hCG | 6 min | 88 min |

In order to evaluate the ability of partially desialylated hCG to induce ovulation in rabbits, intact hCG or 22.5% desialylated hCG were injected intravenously in two separate groups of rabbits.

24 hours after the hCG or desialylated hCG injections, the rabbits were operated, the ovulation points on each ovary were counted and the number of ova recovered from the fallopian tubes was recorded.

As an additional parameter for occurrence of ovulation, progesterone in plasma was determined 24 hours after the injections. Results were as follows:

TABLE

| Hormone | I. U. (biological) | % ovulating | mean No. ovulation points per ovary | mean No. recovered ova | progesterone ng/ml |
|---|---|---|---|---|---|
| intact hCG | 10 | 50 | 5.5 | 5.0 | 0.5 |
| desialylated hCG | 5 | 50 | 3.3 | 1.3 | 0.5 |
| intact hCG | 20 | 81 | 5.1 | 3.4 | 0.8 |
| desialylated hCG | 10 | 67 | 4.7 | 3.0 | 0.5 |
| intact hCG | 40 | 100 | 5.5 | 3.6 | 1.6 |
| desialylated hCG | 20 | 100 | 6.7 | 4.4 | 1.4 |

As can be seen from the date of the above table, desialylated hCG is at least as effective as intact hCG in inducing ovulation in rabbits.

Desialylated hCG has also proven effective in inducing ovulation in women.

One amenorrhoic, MAP (Medroxyprogesterone acetate) — negative, 27 year old patient received one ampoule of 5000 I.U. 25% desialylated hCG after the usual menotropins treatment, when urinary total excretion of estrogens was 274 mcg/day. After a 1-day interval, she received daily one ampoule of 5000 I.U. 25% desialylated hCG for 5 days.

Four days after the first injection, progesterone was 8.7 ng/ml and on the seventh day the progesterone level reached 32 ng. The patient was pregnant, although she aborted in the sixth week. There was no hyperstimulation.

It should be pointed out that the treated patient would not have been suitable for the usual treatment with intact hCG because of the high risk of hyperstimulation that would have followed. The above experiment shows that desialylated hCG is a useful therapeutic means for inducing ovulation when employed in the place of intact hCG in the sequential menotropins-hCG therapy. The pharmaceutical preparations in accordance with this invention are formulated in the form of injectable preparations including:

a. an ampoule containing lyophilized, partially desialylated hCG having a degree of desialylation of 15 to 35%, in an amount corresponding to 5000 I.U. (biological) of hCG, together with one or more excipients such as, for example, lactose; and 2. An ampoule containing an amount of saline sufficient to dissolve the contents of ampoule (1).

The combined contents of the ampoules are suitable for intramuscular or intravenous injection.

I claim:

1. In the method of inducing ovulation by the sequential administration of menotropins and human chorionic gonadotropin, the improvement which comprises employing partially desialylated human chorionic gonadotropin as said human chorionic gonadotropin, wherein said partially desialylated human chorionic gonadotropin has a degree of desialylation of 15 to 35%.

2. The method of claim 1 wherein said partially desialylated human chorionic gonadotropin is administered in an amount of 5000 I.U. human chorionic gonadotropin per day.

3. The method of claim 1 wherein said human chorionic gonadotropin is employed in the form of a saline solution of lyophilized partially desialylated human chorionic gonadotropin.

4. The method of claim 3 wherein said saline solution contains an excipient.

5. The method of claim 4 wherein said excipient is lactose.

* * * * *